US012053075B2

(12) United States Patent
Guizzetti et al.

(10) Patent No.: US 12,053,075 B2
(45) Date of Patent: Aug. 6, 2024

(54) MAKEUP PRODUCT

(71) Applicant: CHROMAVIS S.p.A., Milan (IT)

(72) Inventors: Giorgio Guizzetti, Vimercate (IT); Mauro Gaboardi, Pizzighettone (IT)

(73) Assignee: CHROMAVIS S.p.A., Milan (IT)

( * ) Notice: Subject to any disclaimer, the term of this patent is extended or adjusted under 35 U.S.C. 154(b) by 599 days.

(21) Appl. No.: 17/317,040

(22) Filed: May 11, 2021

(65) Prior Publication Data
US 2021/0353035 A1 Nov. 18, 2021

(30) Foreign Application Priority Data
May 12, 2020 (IT) .................. 102020000010636

(51) Int. Cl.
A61K 8/02 (2006.01)
A45D 33/18 (2006.01)
(Continued)

(52) U.S. Cl.
CPC ............. *A45D 40/00* (2013.01); *A45D 33/18* (2013.01); *B44F 1/02* (2013.01);
(Continued)

(58) Field of Classification Search
CPC .................................... B44F 1/02; A61K 8/02
See application file for complete search history.

(56) References Cited

U.S. PATENT DOCUMENTS 6,296,281 B1 * 10/2001 Stone .................. B42D 25/425
283/93

2016/0030301 A1 * 2/2016 Baracat-Nasr ....... A61K 8/0216
264/328.1
(Continued)

FOREIGN PATENT DOCUMENTS

CN 108014030 A 5/2018
FR 2831778 A1 5/2003
(Continued)

OTHER PUBLICATIONS

English language translation of CN 10814030 A, generated with Espacenet website (https://worldwide.espacenet.com/) on Nov. 22, 2023.*

(Continued)

*Primary Examiner* — Mark Ruthkosky
*Assistant Examiner* — Julia L Rummel
(74) *Attorney, Agent, or Firm* — Dickinson Wright PLLC; Andrew D. Dorisio

(57) ABSTRACT

A make-up product (1) with at least one visible surface (2) on which at least a plurality of basic three-dimensional elements (B) and a plurality of modified three-dimensional elements (M) are obtained, the basic three-dimensional elements (B) being arranged on the surface in a primary pattern (P), in primary rows (P1, P2, . . . ) and mutually side by side, so as to be positioned one after another each on each primary row (P1, P2, . . . ), the modified three-dimensional elements (M) being arranged on the surface in a secondary pattern (S), in secondary rows (S1, S2, . . . ) and mutually side by side, so as to be positioned one after another on each secondary row (S1, S2, . . . ), the secondary pattern (S) replacing the primary pattern (P)—and therefore interrupting it—in some parts of the surface (S) so as to form a figure (F) which is visible when lit from predefined angles.

15 Claims, 4 Drawing Sheets

(51) Int. Cl.
  *A45D 40/00* (2006.01)
  *B44F 1/02* (2006.01)
  *A61Q 1/06* (2006.01)
  *A61Q 1/08* (2006.01)
  *A61Q 1/12* (2006.01)

(52) U.S. Cl.
  CPC ............... *A45D 2040/0012* (2013.01); *A45D 2040/0025* (2013.01); *A61K 8/02* (2013.01); *A61Q 1/06* (2013.01); *A61Q 1/08* (2013.01); *A61Q 1/12* (2013.01)

(56) References Cited

U.S. PATENT DOCUMENTS

| | | |
|---|---|---|
| 2016/0031129 A1 | 2/2016 | Larceri |
| 2016/0066595 A1* | 3/2016 | Grolimund ............... B44F 1/02 426/104 |

FOREIGN PATENT DOCUMENTS

| | | |
|---|---|---|
| KR | 200453355 Y1 | 4/2011 |
| WO | 2019199037 A1 | 10/2019 |

OTHER PUBLICATIONS

Christine, "Guerlain Sun in the City Collection for Spring/Summer 2012", 2012, p. 1-7, https://www.temptalia.com/guerlain-sun-in-the-city-collection-for-springsummer-2012/.*

* cited by examiner

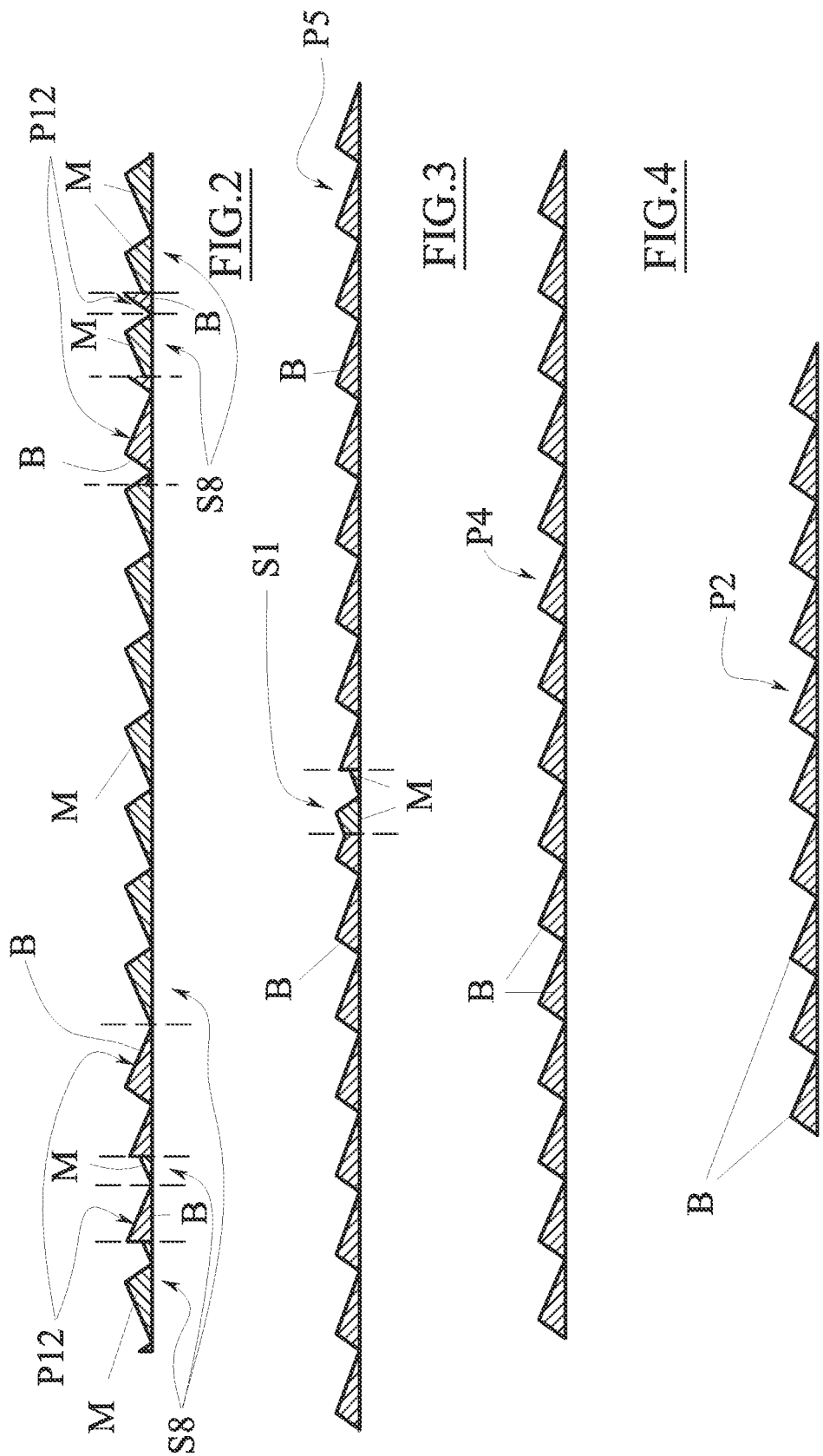

MAKEUP PRODUCT

This application claims priority to Italian Patent Application for Invention No. 102020000010636, filed on May 12, 2020, the disclosure of which is incorporated herein by reference.

FIELD OF THE INVENTION

The present invention relates to a make-up product.

BACKGROUND ART

As it is known, make-up products are aimed at a demanding public. Without detracting from the intrinsic quality of the make-up product, the aesthetic factor plays a fundamental role in the end-user's choice thereof.

SUMMARY OF THE INVENTION

The object of the present invention is to provide a make-up product with an attractive, innovative appearance.

This and other objects are achieved by means of a make-up product according to the technical teachings of the claims annexed hereto.

BRIEF DESCRIPTION OF THE FIGURES

Further features and advantages of the innovation will become clearer in the description of a preferred but not exclusive embodiment of the device, illustrated—by way of a non-limiting example—in the drawings annexed hereto, in which:

FIGS. 2, 3, 4, and 5 are simplified sections taken, respectively, along lines II-II, III-III, IV-IV, and V-V in FIG. 1A;

DETAILED DESCRIPTION OF THE INVENTION

Figure 1:
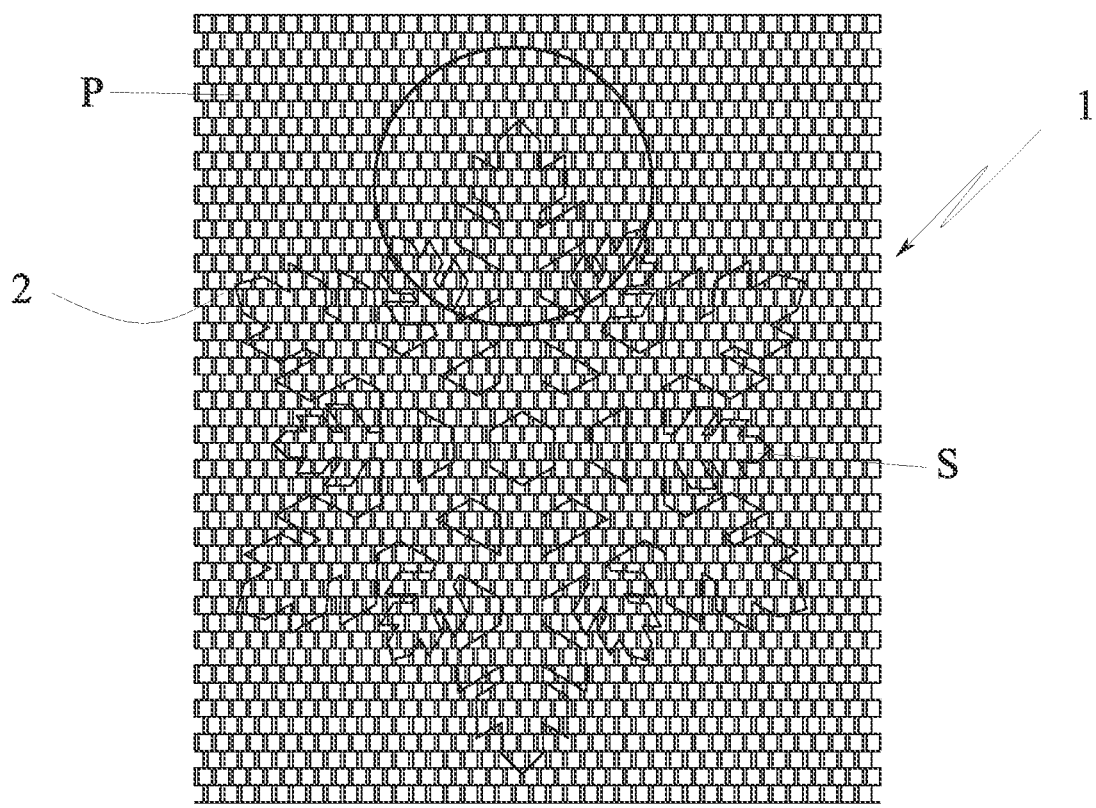
FIG. 1 is a plan view of the writing surface of a make-up product according to the present invention.

With reference to the figures stated, reference number 1 is used to denote, as a whole, a make-up product, and specifically the writing surface thereof is denoted 2.

The make-up product 1 may be for example a lipstick, a compact powder cosmetic product, a cast product, a baked product etc.

The said product comprises at least one visible writing surface 2 on which at least a plurality of basic three-dimensional elements B and a plurality of modified three-dimensional elements M are formed.

Writing surface 2 is the surface from which the end-user takes the make-up product, either directly or by means of an appropriate applicator, for make-up operations.

The surface 2 may more specifically be defined a 'writing' surface. This means that the user, directly of with an applicator, may remove a tiny part of the material (cosmetic) of which the surface 2 is formed. This part remains directly on the user skin or lips (for example if the make-up product is a lipstick) or remains on the applicator that will be subsequently used to make-up a part of the body (preferably of the face) of the user.

As the writing surface is made is to perform a make-up operation it is substantially opaque.

In this text with the term opaque referred to the writing surface 2, it means that said surface it is not transparent or translucent, even if it can be shiny finished or may contain or be covered by reflecting materials like glitters, pearlescent or sparkling particles etc. normally used in make-up industries.

The three-dimensional base elements B are arranged on the surface to form a primary pattern P, consisting of primary rows P1, P2, . . . , arranged mutually side by side lengthways.

In the drawing, rows P1, P2 etc are shown with the letter P followed by a number, which stands for the row.

The three-dimensional elements B are arranged one after another, side by side, on each primary row P1, P2, . . . .

Figure 1A:
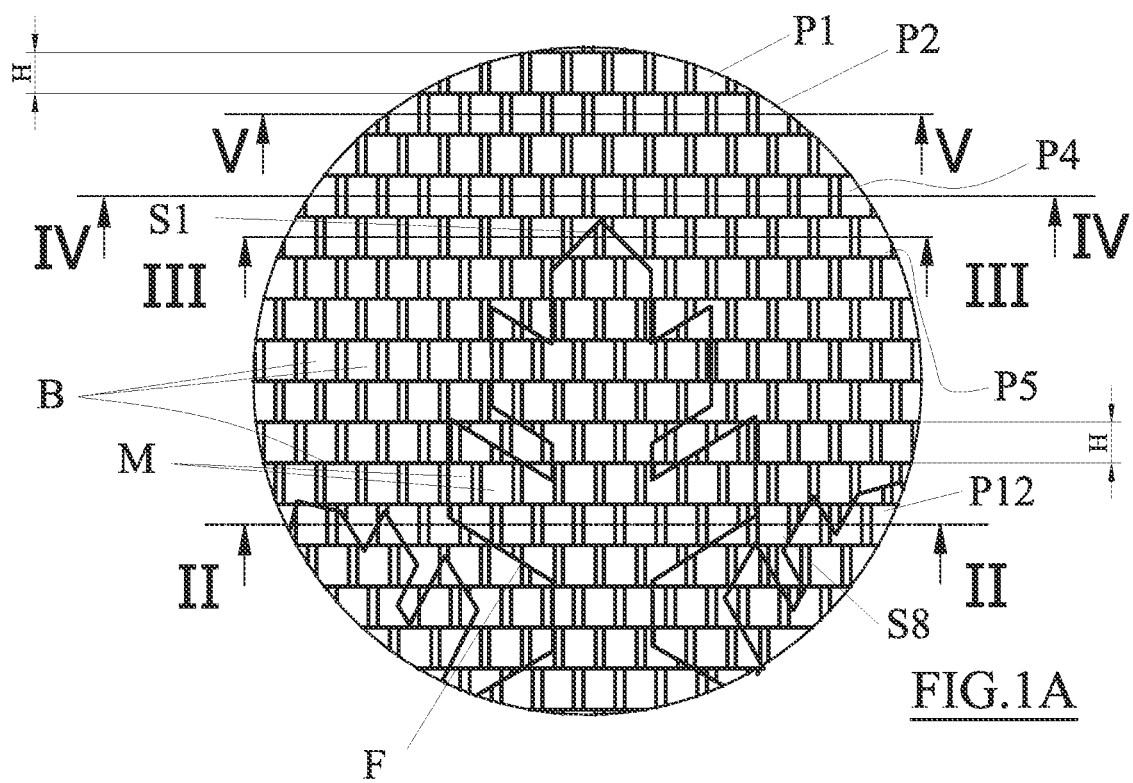
FIG. 1A is an enlarged schematic view of the part circled in FIG. 1.

Between two contiguous rows, the three-dimensional elements are preferably staggered, as is clearly visible in FIG. 1A.

FIGS. 4 and 5 show row P2 and row P4, which are formed entirely of basic three-dimensional elements B, without interruptions. Therefore, row P2 and row P4 are part of the primary pattern.

As regards the modified three-dimensional elements M, these are arranged over the surface 2 so as to form a secondary pattern S and are organised in secondary rows S1, S2, . . . , Within each secondary row S1, S2, . . . , the modified three-dimensional elements M are positioned one after another, side by side The modified three-dimensional elements may be staggered in contiguous sub-rows.

As is clearly visible in FIG. 1, the secondary pattern S interrupts the primary pattern P and replaces it (on the same row) in some parts of the surface S to form a figure F (which, in the case shown in FIG. 1, is a stylised snowflake or snow crystal).

Reference will now be made to FIGS. 2 and 3 in order to better understand how the modified three-dimensional elements M 'replace' the basic three-dimensional elements on the same row.

FIG. 3 shows row P5 of the primary pattern P. In an essentially central portion (of the drawing), the main pattern P is replaced by modified three-dimensional elements M. These are part of the secondary pattern S, and more specifically, of the row denoted S1 here. It can be seen that the modified three-dimensional elements are rotated (in this configuration) by 180 degrees with respect to those of the primary pattern. In the drawing in FIGS. 2 and 3, dashed vertical lines are used to show exactly where the primary or secondary pattern is present.

Similarly to FIG. 3, FIG. 2 shows row P12 of the primary pattern (which is only clearly visible in certain small portions in FIG. 2) with the basic three-dimensional elements B clearly highlighted. In the said row P12, there are essentially more modified three-dimensional elements M than the basic three-dimensional elements B (in order to appropriately delineate figure F).

Obviously, all the three-dimensional elements B of the base pattern may be orientated in the same way, as is easily understood by comparing FIGS. 2-5.

As stated earlier, the primary pattern P is interrupted by the secondary pattern S, and in particular by row S8, which features modified three-dimensional elements M.

In the secondary pattern S, the modified three-dimensional elements M are also oriented in the same way.

Advantageously, the primary pattern P may help to conceal the figure F, when it is not hit by the light from a direction that makes it visible.

Figure F and/or the further figure UF (which will be described below) may include or feature a drawing and/or a logo and/or writing and/or a letter and any other suitable graphic sign, with which one wishes to decorate the surface 2.

Advantageously, the modified three-dimensional elements M are identical to the basic three-dimensional elements B but angled differently on the same row.

Figure 6:
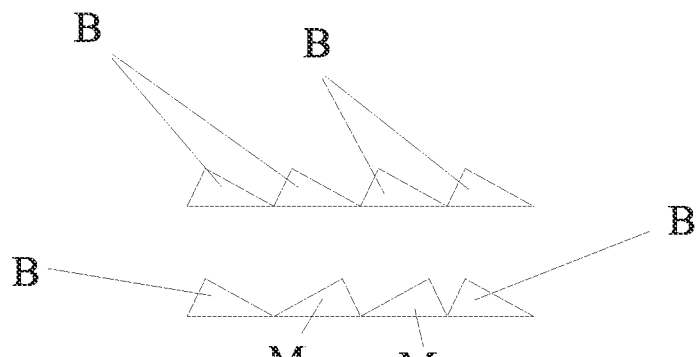
FIG. 6 is a simplified schematic view of a detail of the surface of the make-up product in FIG. 1.

For example, in the solution shown in FIG. 1—which is more understandable when examined with the analysis of FIG. 6 (which is an even more simplified view)—one can see that the modified three-dimensional elements M are rotated by 180 degrees with respect to the basic three-dimensional elements B, even though they are essentially identical.

This way, the light coming from the observer's viewpoint makes the primary pattern or the secondary pattern stand out more or less depending on the angle from which the surface 2 is viewed, making the figure formed from the secondary pattern either stand out or not (the figure is therefore only visible from some angles).

Figure 9:
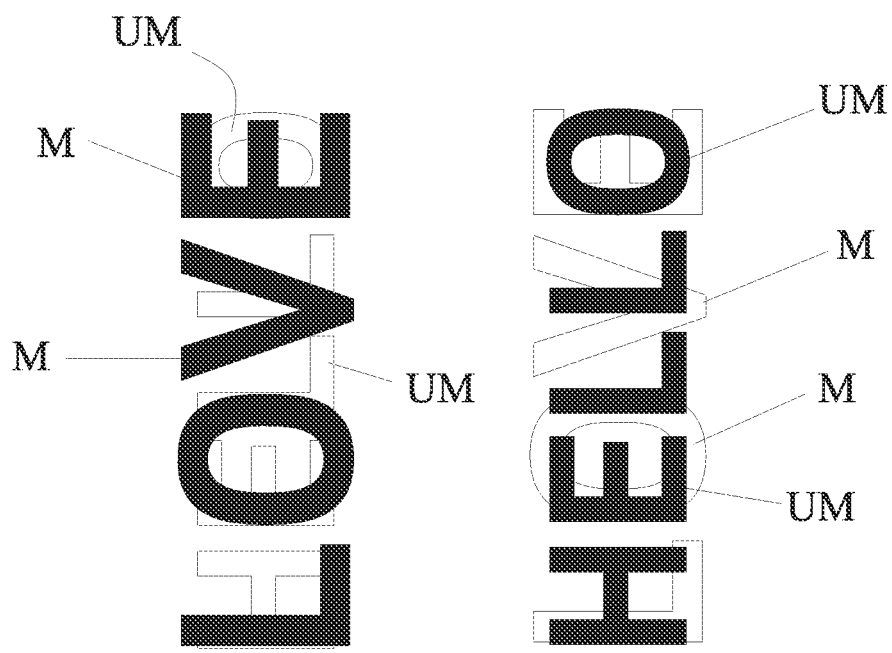
FIG. 9 is a visual effect created by means of a different possible configuration of the surface of the make-up product, as a result of which the right- or left-hand decoration in the figure stands out depending on the viewing angle.
Figure 10:
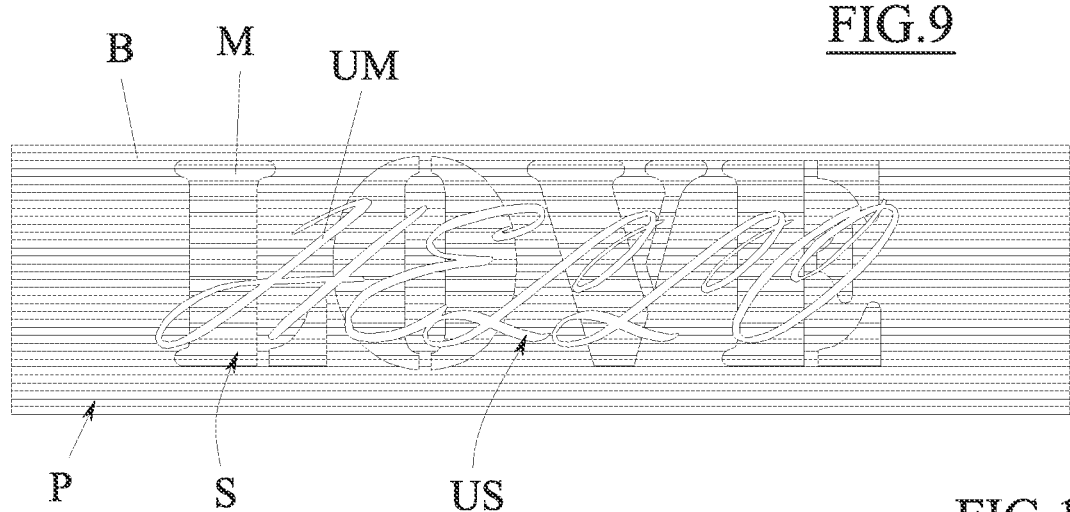
FIG. 10 is a further different possible configuration of the surface of the make-up product, wherein various effects are highlighted—all together for the sake of illustration—which can each be seen on the surface individually depending on the viewing angle.

Advantageously, a plurality of further modified three-dimensional elements UM can be envisaged on the same surface 2, (see FIG. 9 or 10, which is very simplified).

These further modified three-dimensional elements UM are arranged on the surface in a further secondary pattern, organised in further secondary rows, positioned mutually side by side, one after another, on each further secondary row.

The further secondary pattern replaces the primary pattern P and/or the secondary pattern S, in some parts of the surface 2 so as to form a further figure (which, for example, in FIG. 9, is the word 'HELLO' in uppercase normal font, while in the FIG. 10, it is the word 'HELLO' in uppercase italic font.

The further figure is therefore visible from still different angles with respect to those in which only the primary pattern or the figure formed from the secondary pattern is visible.

Essentially, therefore, that stated for the modified three-dimensional elements M also applies to the further modified three-dimensional elements UM, which can be identical to the basic three-dimensional elements B but positioned at a further different angle on the rows of the further secondary pattern.

For example, the modified three-dimensional elements M can be rotated by 180 degrees with respect to the basic three-dimensional elements B, while the further modified three-dimensional elements UM can be rotated by 60 degrees with respect to the basic elements.

Figure 7:
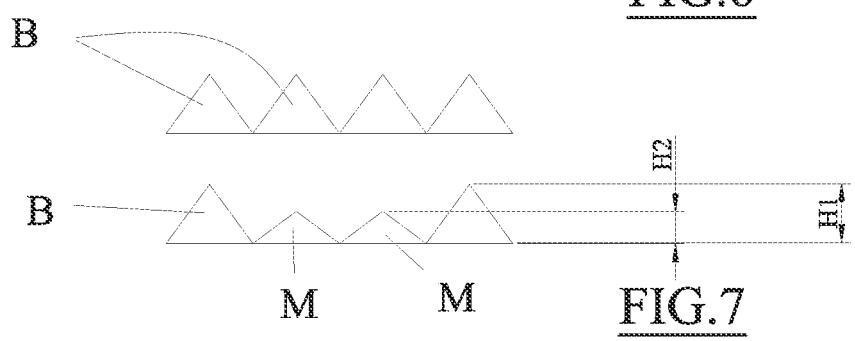
FIG. 7 is a simplified schematic view of a different embodiment of the surface of the invention in FIG. 1.
Figure 8:
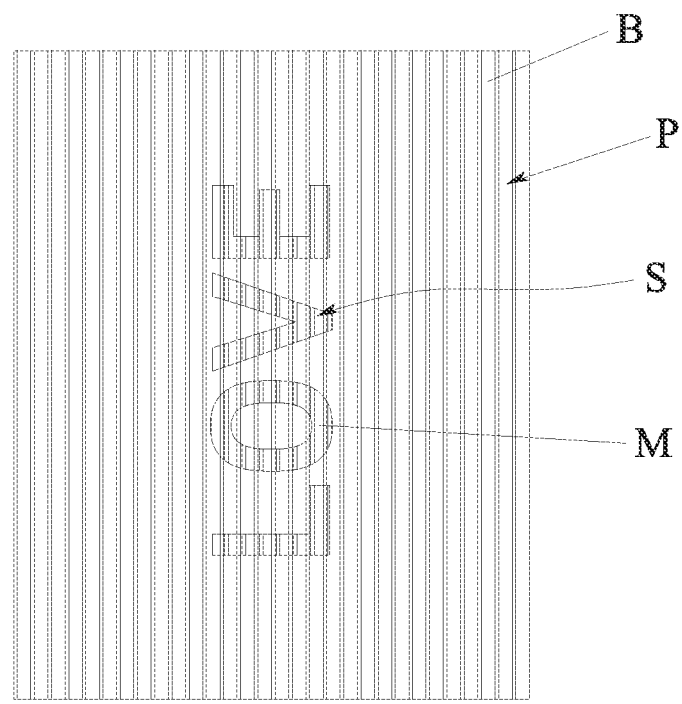
FIG. 8 is an exemplary view of a possible configuration of a surface of a make-up product.

From the various experiments it can be seen that the modified three-dimensional elements M and/or the further modified three-dimensional elements UM can also be made with a height H2 which differs from the height H1 of the basic three-dimensional elements B. This possibility is shown in FIG. 7.

The first row (in the upper part) features only basic elements (and is therefore part of the primary pattern), while the second row includes basic elements B interspersed with modified elements M (and therefore the highlighted row features both the primary and the secondary pattern).

Hence, for example, the modified three-dimensional elements M and/or the further modified three-dimensional elements UM are similar in a geometric sense, and/or have an essentially similar configuration to the basic elements B.

In one possible configuration, such as that shown in FIG. 1 or 1A, the three-dimensional elements B, M, have an essentially prismatic conformation with a triangular base, with two inclined faces of the prismatic elements being exposed on the said surface 2.

The further modified three-dimensional elements UM may also have the same configuration as the one described above.

Furthermore, the exposed faces—on the surface 2—of each three-dimensional element B, M, UM may have a different surface area, due—for example to the prismatic configuration with triangular bases.

Preferably, the primary rows P1, P2 and the secondary rows S1, S2 and/or the additional secondary rows US1, US2 are the same height H, since the secondary pattern or the further secondary pattern must be able to replace the primary patter P (on the same row) perfectly.

Obviously, as already said, the surface 2 may be that of any make-up product.

Figure 11:
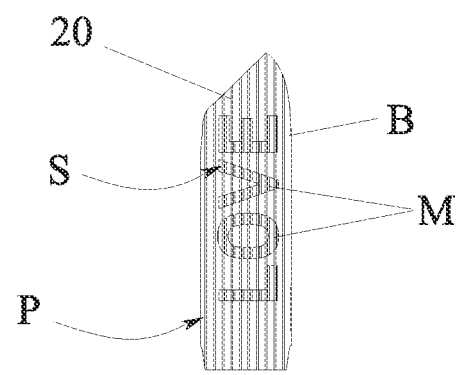
FIG. 11 is a side view of one type of make-up product.

FIG. 11 shows how the surface may be that of a stick product for lips 20, e.g. a lipstick.

For the production of this kind of make-up product, a metal master model is created which features an exact reproduction of the desired surface (for example, produced by electrical discharge machining, milling, or any other suitable mechanical processing system).

The master model is used to create the female mould, for example made of silicone, into which the cosmetic paste (which, once solidified, will form the stick product for lips) is hot-poured.

If, on the other hand, the product is a pressed powder inside a godet, or an extrusion, the raw surface of the make-up product may undergo one or more final pressings by means of a die (always preferably made of metal) with the 'negative' image to be imprinted on the surface of the make-up product engraved thereupon in order to create the three-dimensional elements on the said die as described above.

Various embodiments of the innovation have been described, but others may be conceived using the same innovative concept.

The invention claimed is:

1. A make-up product (1) comprising at least one visible writing surface (2) on which at least a plurality of three-dimensional basic elements (B) and a plurality of three-dimensional modified elements (M) are present, wherein the three-dimensional basic elements (B) are arranged on the writing surface according to a primary plot (P) and organized in primary rows (P1, P2, . . . ), placed side-by-side, the basic elements (B) following each other within each primary row (P1, P2, . . . ), and each of the three-dimensional basic elements includes an inclined first upper surface oriented at a first angle with respect to the writing surface;

wherein the three-dimensional modified elements (M) are arranged on the writing surface according to a secondary plot (S) and organized in secondary rows (S1, S2, . . . ), placed side-by-side, the modified elements (M) following each other within each secondary row (SI, S2, . . . ), and each of the three-dimensional modified elements includes an inclined second upper surface oriented at a second angle with respect to the writing surface;

wherein the secondary plot (S) replaces the primary plot (P), thus interrupting it, in some parts of the writing surface (S);

wherein a combination of the first upper surfaces oriented at the first angle and the second upper surfaces oriented at the second angle forms a visible figure (F) when light illuminates the writing surface from predefined angles and does not form the visible figure when light illuminates the writing surface from angles other than the predefined angles; and wherein the writing surface (2) is a surface used by an end user by picking up part of the material composing the said writing surface to perform a make-up operation.

2. The make-up product according to claim 1, wherein said writing surface (2) is opaque.

3. The make-up product according to claim 1, wherein the surface (2) comprises a plurality of further modified three-dimensional elements (UM), the further modified three-dimensional elements (UM) being arranged on the surface according to a further secondary plot and organized in further secondary rows placed side-by-side, the further modified three-dimensional elements (UM) following each other in each further secondary row, the further secondary plot replacing the primary plot (P) and/or the secondary plot (S) in some parts of the surface (2), so as to form an additional figure.

4. The makeup product according to claim 3, in which the additional figure includes a drawing or a logo or an inscription or a letter.

5. The make-up product according to claim 1, wherein the modified three-dimensional elements (M) are identical to the basic three-dimensional elements (B) but arranged on the surface (2) with a different angle within the rows.

6. The make-up product according to claim 1, wherein the modified three-dimensional elements (M) have different heights with respect to the basic three-dimensional elements (B).

7. The make-up product according to claim 6, wherein the modified three-dimensional elements (M) are geometrically similar to the basic elements (B).

8. The make-up product according to claim 1, wherein the three-dimensional basic elements (B) and the three-dimensional modified elements (M) have a substantially prismatic triangular-based conformation, wherein the three-dimensional basic elements include the first upper surface and a first secondary surface, and wherein the three-dimensional modified elements include the second upper surface and a second secondary surface.

9. The make-up product according to claim 8, wherein the first upper surface and the first secondary surface have different areas, and wherein the second upper surface and the second secondary surface have different areas.

10. The make-up product according to claim 3, wherein the primary rows (P1, P2, . . . ) and the secondary rows (S1, S2, . . . ) or the further secondary rows have the same height (H).

11. The make-up product according to claim 1, wherein the writing surface (2) is that of a lipstick or a compacted powder product or a cast product or a cooked product.

12. The makeup product according to claim 1, in which the figure (F) includes a drawing or a logo or an inscription or a letter.

13. The make-up product according to claim 3, wherein the further modified three-dimensional elements (UM) have different heights with respect to the basic three-dimensional elements (B).

14. The make-up product according to claim 3, wherein the further modified three-dimensional elements (UM) are geometrically similar to the basic elements (B).

15. The make-up product according to claim 3, wherein the further modified three-dimensional elements (UM) are identical to the basic three-dimensional elements (B) but arranged on the surface (2) with a different angle within the rows.

* * * * *